US010215720B2

(12) United States Patent
McGushion

(10) Patent No.: US 10,215,720 B2
(45) Date of Patent: Feb. 26, 2019

(54) RESONANT ELECTROMAGNETIC SENSOR AND INSPECTION SYSTEM

(71) Applicant: Kevin D. McGushion, Simi Valley, CA (US)

(72) Inventor: Kevin D. McGushion, Simi Valley, CA (US)

( * ) Notice: Subject to any disclaimer, the term of this patent is extended or adjusted under 35 U.S.C. 154(b) by 0 days.

(21) Appl. No.: 15/284,338

(22) Filed: Oct. 3, 2016

(65) Prior Publication Data

US 2017/0023501 A1 Jan. 26, 2017

Related U.S. Application Data

(63) Continuation of application No. 14/472,253, filed on Aug. 28, 2014, now Pat. No. 9,459,237, which is a continuation-in-part of application No. 13/396,378, filed on Feb. 14, 2012, now abandoned.

(60) Provisional application No. 61/442,742, filed on Feb. 14, 2011.

(51) Int. Cl.
| | |
|---|---|
| *G01R 33/12* | (2006.01) |
| *G01N 24/08* | (2006.01) |
| *G01N 27/72* | (2006.01) |
| *G01N 29/275* | (2006.01) |
| *G01N 29/22* | (2006.01) |
| *G01R 33/022* | (2006.01) |
| *G01R 33/028* | (2006.01) |

(52) U.S. Cl.
CPC ............ *G01N 24/08* (2013.01); *G01N 27/72* (2013.01); *G01N 29/225* (2013.01); *G01N 29/275* (2013.01); *G01R 33/022* (2013.01); *G01R 33/028* (2013.01); *G01R 33/1253* (2013.01)

(58) Field of Classification Search
CPC  G01R 33/028; G01R 33/022; G01R 33/1253; G01N 29/225; G01N 29/275
USPC .......................................... 324/239
See application file for complete search history.

(56) References Cited

U.S. PATENT DOCUMENTS

| | | | | |
|---|---|---|---|---|
| 3,612,987 A | * | 10/1971 | Placke ............... | G01N 27/9013 324/242 |
| 4,596,953 A | * | 6/1986 | Nagasaka .......... | G01N 27/9013 324/207.25 |
| 5,196,664 A | * | 3/1993 | McGushion ........... | B23K 9/325 219/60 A |
| 5,422,456 A | * | 6/1995 | Dahm .................. | B23K 26/103 219/121.63 |
| 2005/0253711 A1 | * | 11/2005 | Nelson ................. | F41H 11/136 340/552 |

(Continued)

*Primary Examiner* — Melissa Koval
*Assistant Examiner* — Courtney McDonnough
(74) *Attorney, Agent, or Firm* — Aaron McGushion

(57) ABSTRACT

The present device relates to a sensor capable of detecting changes in the electromagnetic field it generates when in proximity to either conductive or nonconductive materials. This occurs by way of oscillating a transmit coil with an electro motive force at a resonant frequency thus creating an electromagnetic field. The magnetic field passes through a target of either conductive or nonconductive material and is then intercepted by a receive coil which likewise oscillates at a resonant frequency, which when in proximity to the transmit coil and transmit coils resonant frequency produces an enhanced signal by way of the interaction of the respective resonant frequencies and receive coil output.

11 Claims, 13 Drawing Sheets

(56) References Cited

U.S. PATENT DOCUMENTS

2006/0060631 A1* 3/2006 Frasch ................. B23K 20/004
 228/4.5
2010/0275694 A1* 11/2010 Roberts .................... F17D 5/00
 73/637

* cited by examiner

RESONANT ELECTROMAGNETIC SENSOR AND INSPECTION SYSTEM

RELATED APPLICATION DATA

This application is a continuation of co-pending U.S. application Ser. No. 14/472,253 filed Aug. 28, 2014, which is a continuation-in-part of co-pending U.S. application Ser. No. 13/396,378 filed on Feb. 14, 2012, which, in turn, claims the priority date of Provisional Application for Patent No. 61/442,742 filed on Feb. 14, 2011, each of which are incorporated by reference in their entirety.

BACKGROUND

The present device relates to a sensor capable of detecting changes in the electromagnetic field it generates when in proximity to either conductive or nonconductive materials and a device for orbiting about the joint between two tubular components for inspecting the welded or joined joint.

There has been a persistent need to inspect both conductive and nonconductive items for consistency and for the presence of flaws with a single technology capable of overcoming deficiencies associated with traditional x-ray, eddy current, ultrasonic and other nondestructive inspection methods currently employed. The problem with x-ray has been the dangerous nature of the high energy electromagnetic wave and the hazards to biological organisms are well understood, given this and the need for elaborate shielding, x-ray can be very undesirable. Also, while x-ray is useful for detecting volumetric anomalies such as voids or the presence of foreign objects, flaws such as cracks where the adjoining faces of the cracks may be in intimate contact and having no appreciable volume, are very difficult to detect.

Standard eddy current inspection is useful in detecting discontinuities in metal and other conductive materials, but do not work well when inspecting nonconductive materials. The inability to inspect nonconductive materials has limited eddy current applications. Eddy current inspection may also employ design features which allow the effects of signal output due to changes in liftoff (the distance between the sensor and the item) to be inspected to be mitigated. These design features are permanent and may not be changed on the fly during inspection, thus limiting its ability to instantaneously determine liftoff.

Ultrasonic inspection can be difficult to employ, given the need to provide a coupling fluid or gel to transmit the ultrasonic frequency from a transducer to a target being inspected. It is often impractical to use such coupling fluids and gels on many structures as well as completed structures such as can be expected in the air frame of a finished aircraft, especially when constructed of composite. Also, it is not possible to use ultrasonic inspection technologies when there is an air gap separating otherwise inspectable walls, as air lacks the necessary transmissive qualities associated with a coupling fluid.

Furthermore, the problem of inspecting small orbitally welded systems comprised of at least two components, each having at least one tubular extension meant to convey fluid with the extensions being orbitally welded one to the other, has been one of accessibility and motion control. Orbitally welded assemblies are generally comprised of at least two components, each component having at least one tubular element extending from the component for conveying fluid. The tubular elements of at least two components are connected one to the other by way of orbital welding such as the orbital welding method described in McGushion U.S. Pat. No. 5,196,664.

Motion control is required to precisely place a sensing means over a weld joint and move the sensing means rotatably, and at times translationally, around the central axis of the weld joint in order to accomplish a complete inspection of the joint, areas adjacent to the joint, and areas in transition with the joint (known as the heat affected zone) in the smallest envelope possible.

To inspect the above type of joint, a motion control system must also be able to transport a sensing means around a joint while avoiding impact or other mechanical interference with other components in the orbitally welded assembly. Orbitally welded components are often in close proximity to the joint being inspected as might be expected in the tight confines of a propulsion system of a satellite, rocket, or the hydraulic system of a fighter or commercial jet. In these tight applications, densely configured fluid control systems are often made with the prerequisite need to economize both size and weight. It is also necessary to transmit the data collected with such an inspection means to a computer controlled processing means and graphical interface so that the sensing means signal output may be correlated to a precise location on the welded joint in graphical form which can then be easily interpreted.

Previous attempts to image these sorts of orbital welds have almost exclusively been done with an x-ray means, either with the use of film, computer tomography (CT), digital real-time radiography (digital RTR). The use of x-rays creates a safety hazard, where the work area must be evacuated and lead shielding employed. While x-ray inspection is well suited to discovering volumetric flaws such as porosity or inclusions of foreign objects in the weld, they are ill suited for discovering flaws, such as cracks which have very little volume. Additionally, x-ray inspection is time consuming, often requiring the orbital weld assembly to be removed from manufacture and brought to an x-ray booth. X-ray inspection often requires secondary methods to be used in order to effectively detect cracks which may not have been otherwise visible. The secondary method of inspection is generally a dye penetrant inspection, where fluorescing liquid is applied to the surface of the weld causing any existing surface cracks or imperfections to be filled with minute quantities of the liquid, which when illuminated by a type of light source, reveals the surface cracks or imperfections. The penetrant method requires a time consuming post inspection cleaning to remove the liquid. For these reasons, both x-ray and dye penetrant are inadequate to the task.

Other inspection technologies, such as eddy current sensors, eddy current sensor arrays, ultrasonic sensors, ultrasonic sensor arrays, and thermographic inspection, are capable of inspecting orbitally welded joints for evidence of surface and subsurface defects, and possess the necessary miniaturization of the sensor technology itself to inspect tightly configured orbital welds. However, each of the above inspection methods lack the combination of sufficient miniaturization and sophistication in motion control, to transport the sensor precisely and repeatedly in order to inspect a weld in the confined space of a fluid assembly that has been orbitally welded.

Accordingly, there is a need for a sensor which does not produce harmful radiation, which can inspect conductors and nonconductors alike and can inspect through walls of various materials and air gap transitions. Such a sensor should be very compact to allow easy access to confined spaces and should also allow for inspection of small features and anomalies which may be critical to the performance of the item or system being inspected. The sensor should provide an output that has signal variation relative to varying features or anomalies of a target and which may be located in the item being inspected. The sensor should have the ability to control for variables such as liftoff or material changes without the need to make permanent physical changes to the sensor.

Furthermore, there is a need for a system with a sensing means capable of inspecting cracks, volumetric flaws and other defects on and in orbital tube welds which can be rotatably transported around the central axis of a weld joint and adjacent areas, so that a complete analysis of the weld area may be made, revealing defects and cracks. Additionally, a motion control system capable of transporting a sensing means is needed, that is suitably compact to allow placement and use in areas of tight configuration within an orbitally welded assembly, where other components of that assembly may be present and in close proximity to the area being inspected. This motion control system must lend itself to rapid installation onto and removal from the joint being inspected. Such a system must also communicate its sensing means output or data to a computerized controller for graphical presentation and interpretation of data.

SUMMARY

The present resonant electromagnetic sensor provides an enhanced signal output by utilizing a transmit coil which resonates at a fixed or series of resonant frequencies. When an electro motive force (EMF) at resonant frequency or frequencies is induced to the transmit coil, it generates an electromagnetic field which oscillates relative to the frequency applied. This electromagnetic field passes through a target of either conductive or nonconductive material; and is then intercepted by a receive coil which also resonates at a frequency or series of frequencies in strategic proximity to the resonant frequency or frequencies of the transmit coil. The receive coil, by way of Lenz's Law converts the intercepted oscillating magnetic field and converts it to a signal which can be analyzed to reveal subtle and gross changes in the material being inspected. The proximity of the frequencies of the transmit and receive coils is meant to maximize sensor output by way of high 'Q' or quality factor and of high output signal which occurs when the transmit and receive coils have been tuned and brought into proximity to one another.

The present sensor also provides frequencies at which the effects of liftoff and/or target material change may be mitigated if the transmit and receive coils have been appropriately tuned. Because of its high 'Q' and output signal, the present sensor is very sensitive to not only the subtle changes that may exist in a target of conductive material, but nonconductive material as well, so that it may scan from one type of material to the next without the need for sensor changes. Because of its unique "tuning" ability by way of adjusting resonant frequencies of transmit and receive coils, the present sensor may neglect the effects of liftoff and or changing materials under the sensor in order to generate a more complete image of the material being inspected. The present sensor is also capable of scanning through multiple walls of materials, with air and other materials at the transition boundary between the walls, and resolve characteristics not only of the intermediate walls but of the wall on the far side as well.

Additionally, an orbital weld inspection system provides a motion control system with eddy current type sensing means and accurately controls both rotational motion around a joint and axial motion across the joint when necessary in order to generate a coordinate based output of data, where rotation may be represented as the 'x' axis or polar axis and where the axial distance across the joint may be represented as the 'y' axis and in a Cartesian or polar coordinate system where the signal output may be represented as a third or 'z' axis. This coordinate matched data is communicated to a computerized controller for graphical display and interpretation of said data. The present system also incorporates a means for quickly installing and uninstalling itself on the joint in space with limited clearance.

LISTING OF REFERENCE NUMERALS OF DESCRIBED EMBODIMENTS

Figures 1, 2:
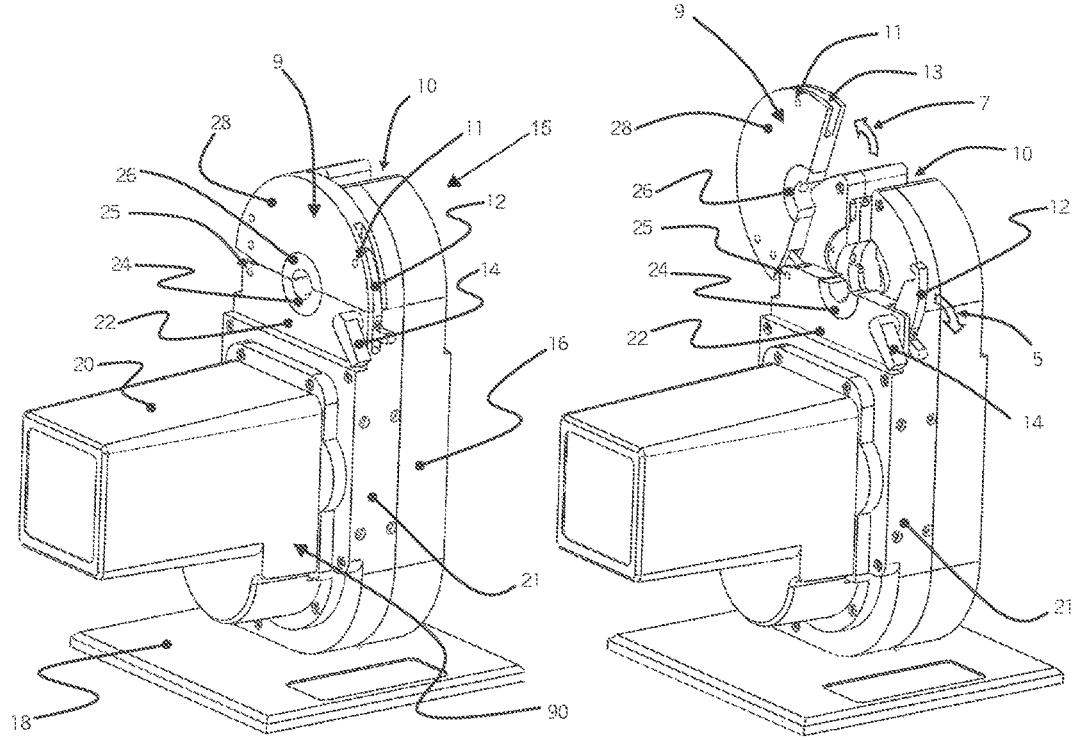
FIG. 1 is an isometric view of the orbital tube weld inspection head constructed in accordance with this specification.
FIG. 2 is an isometric view of the head with the fixturing means open.

Weld Joint Assembly 1
Arrow 5
Arrow 7
Fixture Means 9
Opening 10
Pin 11
Hook 12
Open Portion of the Rotatable Gear 13
Thumb Cam 14
Front Main Housing 16
Pedestal 18
Motor Housing 20
Back Main Housing 21
Fixture Bottom 22
Changeable Collet Type Insert Bottom 24
Fixture Top Hinge Point 25
Changeable Collet Type Insert Top 26
Fixture Top 28
First Component 30
First Path 31
Orbital Weld Joint 32
Second Path 33
Second Component 34
Sensor 36
Rotatable Gear 40
Translation Table Track 41
First Wire Spool 42
Rotor Assembly 43
Linear Glide Bearing 44
Rotor Assembly Groove 45
Combination Rotation and Translation Stepper Motor 46
First Constant Force Spring Spool 48
Slip Ring Capsule 50
Second Wire Spool 52
Rail for Linear Glide Bearing 54
Drive Gear 56
Drive Coupler 58
Translation Table 59
First Set of Tandem Gears 60
Second Set of Tandem Gears 62
Arrow 64
Arrow 66
Constant Force Spring 68
Input and Output Signal and Power Lines 70
Arrow 72
Signal and Power Cable 74
Arrow 76
Arrow 78
Second Constant Force Spring Spool 79
Cable Groove 80
Port for Main Power Signal and Control Cable 82
Strain Relief Toe-Clamp 84
Torsional Spring 86
Sensing Means Pivot Point 87
Arrow 88
Orbital Weld Inspection Head 90
Main Power and Signal Control Cable 92
Controller with Computer and Graphical Display 94
Sensor Assembly 220
First Lead of the Transmit Coil 222
First Lead of the Receive Coil 224
Receive Coil 226
Transmit Coil 228
Core 230
Second Lead of the Receive Coil 232
Second Lead of the Transmit Coil 234
Oscillating Magnetic Field 236
Discontinuity in Target Material 238
Target Material 240
Transmit Coil Circuit 241
Source of Oscillating EMF 242
Receive Coil Circuit 243
Transmit Coil Capacitor 244
Transmit Coil Resistor 246
Resonant Peak 248
Voltage Level at −3 dB 250
Upslope Side of Curve 252
Frequency 1 254
Resonant Frequency 256
Frequency 2 258
Bandwidth 259
Downslope Side of Curve 260
Peak Voltage at Resonant Frequency 262
Receive Coil Resistor 264
Signal Monitoring and/or Conditioning Device 266
Receive Coil Capacitor 268
Transmit Coil Resonant Peak 270
Trough 272
Receive Coil Resonant Peak 274
Transmit Coil Variable Capacitor 276
Transmit Coil First Resonant Peak 278
Transmit Coil Second Resonant Peak 280
Sympathetic Resonant Peak 282
Transmit Coil Fourth Resonant Peak 284
Transmit Coil Fifth Resonant Peak 288
Transmit Coil Sixth Resonant Peak 290
Receive Coil Variable Capacitor 292
Wall Control Frequency 294
Resonant Frequency Shift for Air Gap 296
Air Gap Control Frequency 298
Resonant Frequency Shift for Wall 300
Rectifier Portion of Circuit 302
Amplifier First Stage 304
Amplifier Second Stage 306
Signal Output 308
Offset Input 310
Gain Resistor 312

DESCRIPTION OF THE PREFERRED EMBODIMENTS

Referring to the drawings wherein identical reference numerals denote the same elements throughout the various views. The following description of the resonant electromagnetic sensor is the preferred embodiment when said system is reduced to practice however, it is not intended to be the only embodiment as features and practices may be altered while still remaining within the intent and scope of this specification.

FIGS. 1-4 illustrates the fixturing action of the orbital weld inspection head 90 (which may also be referred to generally as an "orbital device"), where a tube is inserted and in clamped in place. In at least one embodiment, the housing 15 encloses various components and comprises one or more of a front main housing 16, a back main housing 21, and a motor housing 20. FIG. 1 further shows the fixture portion in its closed position with changeable collet type inserts 24 and 26 accommodating various diameters of assemblies to be inspected. Insert 24 are rigidly affixed to the fixture bottom 22 and insert 26 are affixed to the movable fixture top 28 which is hinged at point 25 to allow easy opening and closing, fixture bottom 22 is made as an integral part of head housing 21 for ease of manufacture and fixture top 28 is brought into compressive load by way of hook 12 being engaged in pin 11 and being downwardly loaded toward fixture bottom 22 by the action of thumb cam 14; collectively these elements are referred to as the fixture means 9 or may also be referred to as a fixture 9. The inspection head 90 is mounted on a pedestal 18 for ease of use on a table however, this pedestal may be removed in order to make the head more mobile and allow insertion into complex welded assemblies which may be inspected.

Figures 3, 4:
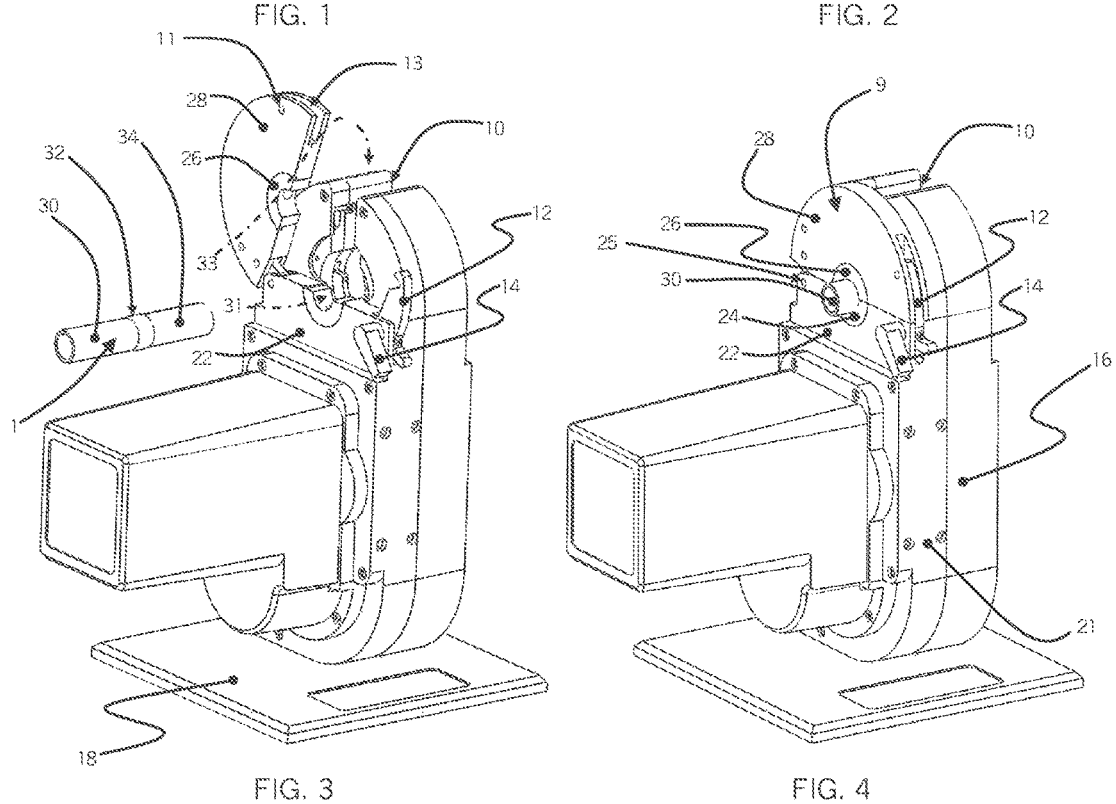
FIG. 3 is an isometric view of the head and fixturing means with a weld joint assembly ready to be inserted in the head and fixturing means.
FIG. 4 is an isometric view of the head with a weld joint assembly inserted into the head and locked in place by the fixturing means.

FIG. 2 illustrates the fixture in its open position, having pivoted hook 12 off pin 11 and out of groove 13 in the direction of arrow 5 by releasing thumb cam 14, fixture top 28 is free to open in the direction of arrow 7 carrying with it insert 26. FIG. 3 illustrates a welded joint assembly 1 having been orbitally welded, joining components with at least a tubular end meant to convey fluid and comprised of at a minimum a first component 30 and a second component 34 joined by orbital weld 32. This welded joint assembly 1 is ready to be inserted into the inspection head 90 and said assembly may be inserted axially in along first path 31 or if the assembly were more complex and attached to other components it may be inserted along second path 33, passing through opening 10 clearing all internal working components of inspection head 90 until it comes to rest on lower insert 24 of fixture means 9.

Figure 5:
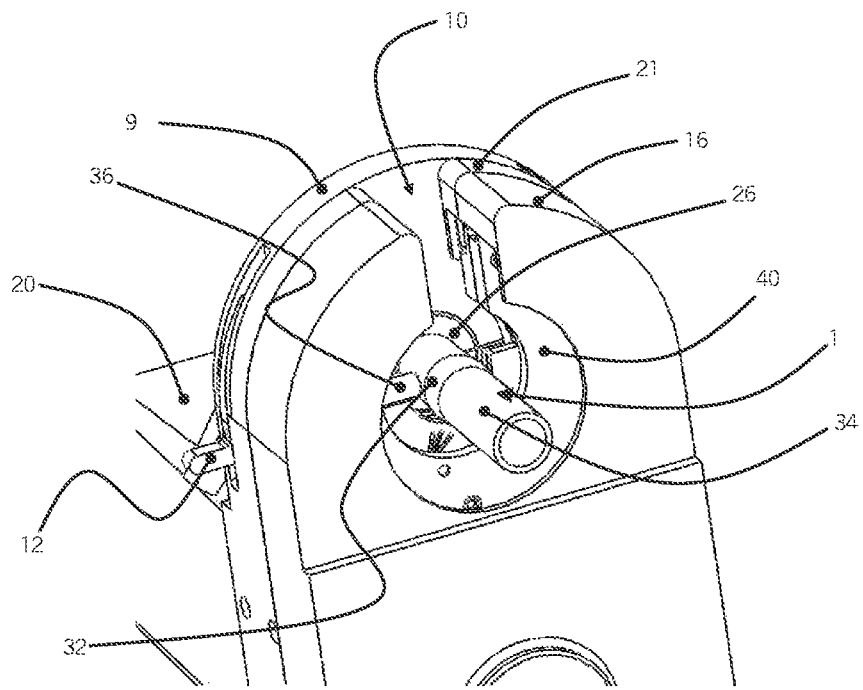
FIG. 5 is an isometric projection of a portion of the head showing the sensing means aligned adjacent to a weld joint.

FIG. 4 illustrates the clamping action of fixture top 28 as it is pivoted downward at pivot point 25 carrying with it insert 26 which is applied against tube 30 and in opposition to insert 24. Hook 12 is reinserted into groove 13 and engages pin 11, then thumb cam 14 is engaged pulling hook 12 downward bringing load to bear on fixture top 28 and insert 26 securely holding the weld joint assembly by clamping tube 30 between inserts 24 and 26. FIG. 5 illustrates the weld joint assembly securely being held by the fixture means 9 such that the sensing means 36 is allowed to be positioned at a point where inspection is to begin. In this embodiment is an eddy current type sensor is used however, other types of sensors may just as easily be substituted for instance an eddy current array, ultrasonic sensor or an ultrasonic array collectively these types of sensor are referred to as the sensing means 36. In some cases the inspection will begin adjacent to the orbital weld joint 32 so as to allow inspection of the heat affected zone or HAZ which is an area of changed metallurgy being brought about by the extreme heat of welding and adjacent to the actual orbital weld joint 32. In other cases the HAZ may not be inspected and the point at which inspection begins may be on the orbital weld joint 32.

Figure 6:
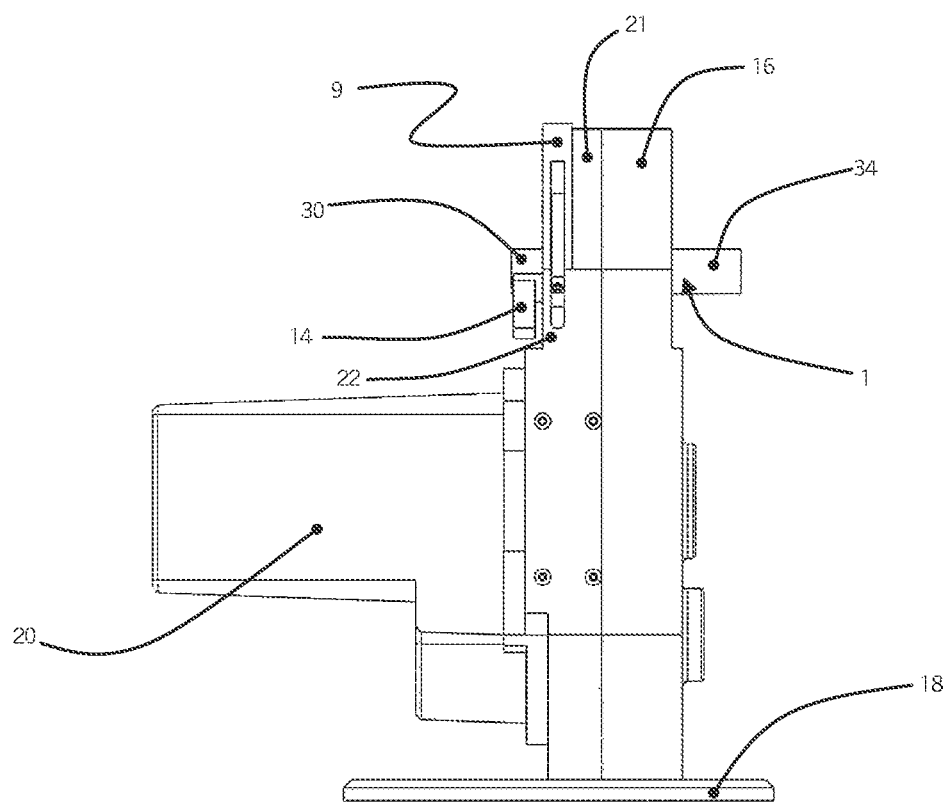
FIG. 6 is a side projection of the head and fixture means.
Figure 7:
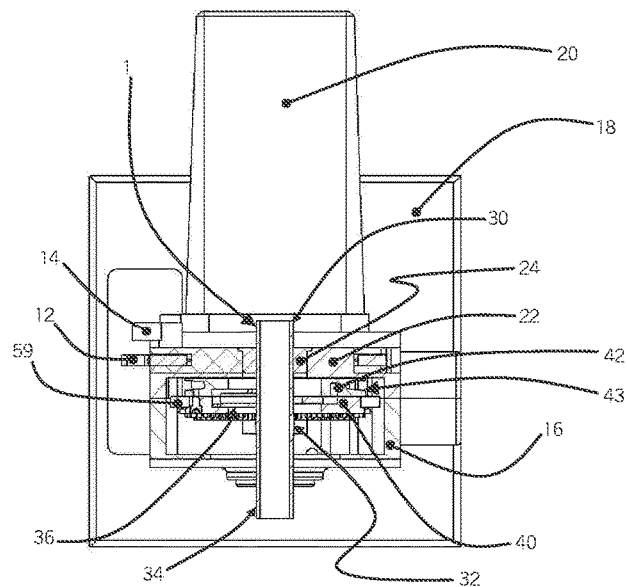
FIG. 7 is a top cross sectional view along line AA of the sensing means, weld joint assembly and fixturing means.
Figure 8:
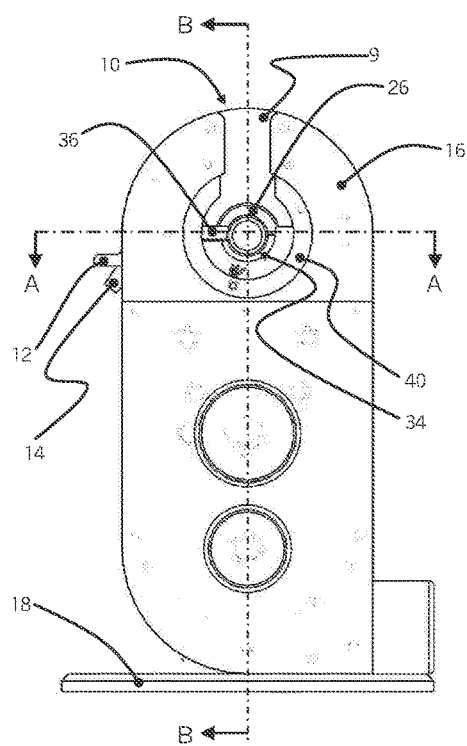
FIG. 8 is a front projection of the head.

FIG. 6 illustrates orbital weld inspection head 90 in side view and with weld joint assembly 1 secured in the fixture. FIG. 7 is a sectional view along the line AA illustrating weld joint assembly 1 being held securely by fixturing means 9 with sensing means 36 positioned to inspect the joint assembly and being held by rotor assembly 43 being comprised of a rotatable gear 40 (which may also be referred to generally as a "rotating member") first wire spool 42 and sensing means 36. FIG. 8 is an illustration of orbital weld inspection head 90 in front view.

Figure 9:
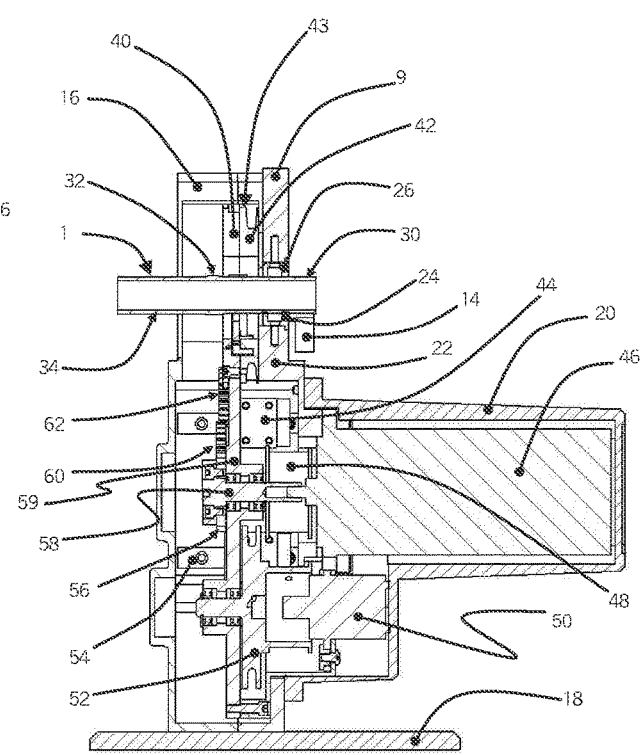
FIG. 9 is a side cross sectional view along line BB of the fixturing means, motion control means and a weld joint assembly.

FIG. 9 is a sectional view along the line B-B of orbital weld inspection head 90 illustrating a motion control system comprised of a translation table 59 (which may also be referred to generally as a "translating member") combination rotation and translation stepper motor 46 drive coupler 58 drive gear 56 first set of tandem gears 60 second set of tandem gears 62 linear glide bearings 44 rails for linear glide bearings 54 second wire spool 52 first constant force spring spool 48 and slip ring capsule 50 where said motor 46 transmits rotational motion to the rotor assembly 43 in discrete steps or at a constant speed by way of driving the main drive gear 56 which then drives first set of tandem gears 60 which then drives second set of tandem gears 62 and where said motor 46 being able to drive both rotatably and translatably also transmits translational motion to the rotor assembly 43 by moving said drive coupler 58 in an axial manner causing translation table 59 which carries said rotor assembly to move translatably.

Figure 10:
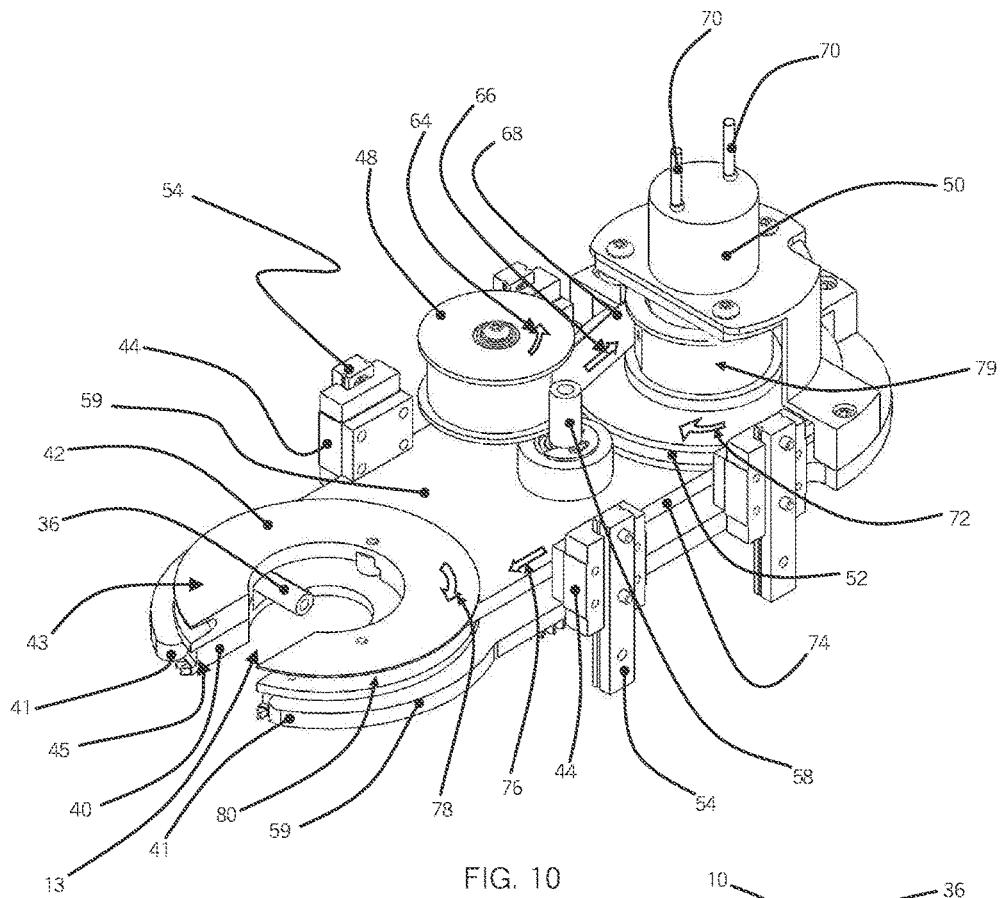
FIG. 10 is an isometric view of a portion of the motion control assembly showing the cable management system and constant force spring return system.
Figures 11, 12:
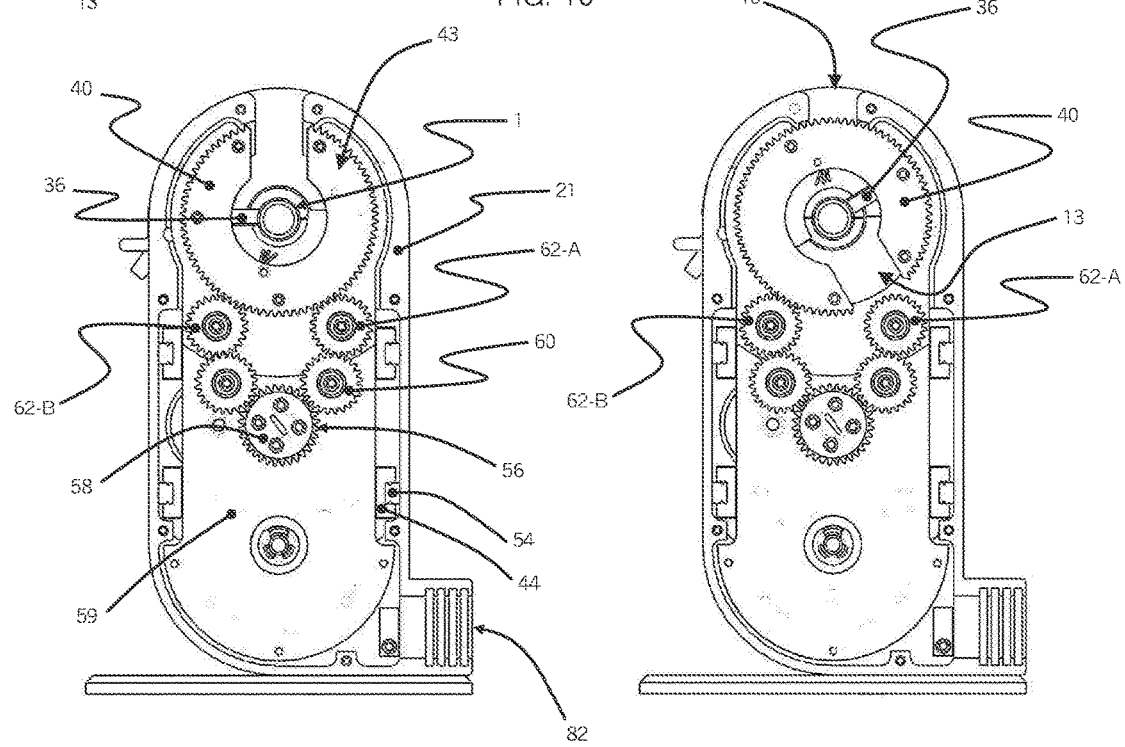
FIG. 11 is a front projection of the head with the cover removed showing the tandem gear drive system.
FIG. 12 is a front projection of the head with the cover removed showing the tandem gear system transitioning past the open portion of the rotatable gear.

FIG. 10 illustrates the internal motion control of the orbital weld inspection head 90 where drive coupler 58 having been rotated by combination rotation and translation motor 46 (not shown in this view) and passing through translation table 59 engages drive gear 56 which is best viewed in FIG. 11. The drive gear 56 having been rotated a prescribed amount or at a fixed speed, first set of tandem gears 60 are driven in turn driving second set of tandem gears 62 which in turn drive rotatable gear 40 of the rotor assembly 43 causing the sensing means 36 to be rotatably moved around weld joint assembly 1 being conducted and restrained by the translation table track 41 being contained in a slip fit fashion by the rotor assembly groove 45.

As the previously described rotation takes place it can be appreciated in FIG. 10 that the signal and power cable 74 is allowed to remain in constant connection with the rotating sensing means 36 and the rotationally stationary portion of the translation table 59 where input and output signal and power lines 70 are located by way of a cable management system comprised of a first wire spool 42 signal and power cable 74 second wire spool 52 second constant force spring spool 79 constant force spring 68 first constant force spring spool 48 and slip ring capsule 50 where as rotor assembly 43 rotates in direction 78 signal and power cable 74 is allowed to wind-up on rotor assembly 43 with signal and power cable 74 lying in cable groove 80. Signal and power cable 74 being donated to the rotational motion of rotor assembly 43 second wire spool 52 serves as a wound reservoir of said signal and power cable 74 sufficient in length to accommodate any expected rotation of the rotor assembly 40. Some tensile pull being required to manage signal and power cable 74 a constant force spring 68 applies a tension load to signal and power cable 74 in the direction of the second wire spool 52 by said constant force spring 68 being wound onto second constant force spring spool 79 and first constant force spring spool 48. Given the natural reaction of the constant force spring 68 to resist extension or being unwound, a constant tension force is applied to the signal and power cable 74 through counter rotation being applied to the second constant force spring spool 79 and the second wire spool 52 respectively. As the rotor assembly 43 rotates back to its original start position the signal and power cable 74 is donated from the first wire spool 42 back to the second wire spool 52 and kept in constant tension to allow organized rewinding by the pulling action of the constant force spring 68. The wound signal and power cable 74 is communicated to the central axis of the second wire spool 52 where it is connected to leads of the slip ring capsule 50 where a brush type contact in the slip ring capsule 50 translates the rotary motion of the second wire spool 52 and signal and power wire 74 to a fixed position at input and output signal and power lines 70 said rotation being given by this action to said sensing means 36 sufficient to rotate past the whole of or a desired portion of the weld joint assembly 1.

The combination rotation and translation stepper motor 46 being capable of linear translation in discrete steps or a constant velocity said motion is connected to the translation table 59 by way connection to the motor with the drive coupler 58 said translation being guided and restrained within the back main housing 21 by linear glide bearings 44 and rails for linear glide bearings 54 with relative motion of the combination rotation and translation motor 46 restrained by being affixed to said back main housing 21 said translation being given by this action to sensing means 36 sufficient to traverse the desired distance across the weld joint assembly 1 and in desired increments or at a constant velocity.

FIG. 12 illustrates the constant drive feature of the tandem gear sets 60 and 62 whereas the rotor assembly 43 rotates and the open portion of the rotatable gear 13 approaches tandem gear 62-A the rotatable gear 40 remains in constant drive contact with tandem gear 62-B during the transition of open portion of the rotatable gear 13 past tandem gear 62-A when the open portion of the rotatable gear 13 has sufficiently traveled, tandem gear 62-A reengages rotatable gear 40 of rotor assembly 43. This action will take place alternately for the second set tandem gears 62 to accommodate any number of full rotations of the rotor assembly 43. The rotation and translation actions having thus been described any combination of these actions may be employed in any increment or series of increments or velocity or velocities and in conjunction with the sensing means output delivered to input and output signal lines 70, sensing means signal output may be correlated so as to match a particular rotational or translational location or series of locations.

Figure 13:
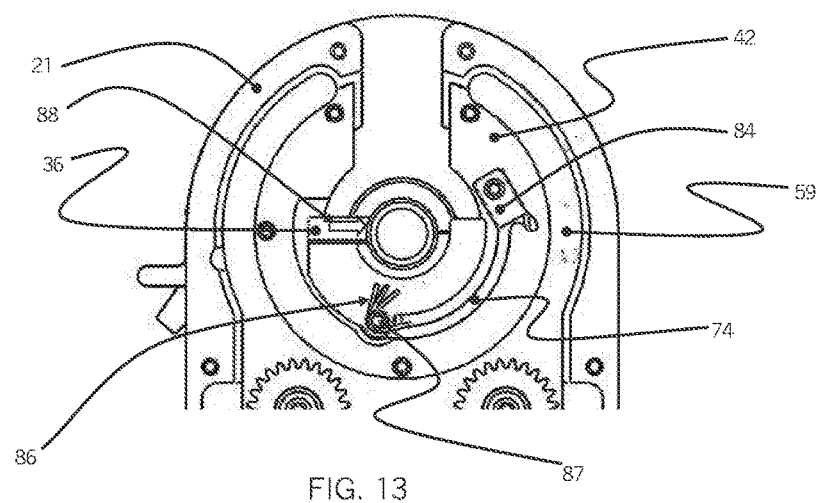
FIG. 13 is a front projection of a portion of the head with the cover removed and gear portion of the rotor removed revealing a holder for the sensing means.

FIG. 13 illustrates the sensing means 36 with rotatable gear 40 removed and being held against weld joint assembly 1 by the rotating action of torsional spring 86 about sensing means pivot point 87 said action causing said sensing means to remain in compliant contact with said weld joint assembly. Signal and power cable 74 within first wire spool 42 being restrained by strain relief toe-clamp 84 against the tensile action of the previously described constant force spring 68 applied to the signal and power cable 74 said tension having been restrained constituent wire of the signal and power cable 74 may be hooked-up to said sensing means for power and signal delivery and transmission.

Figure 14:
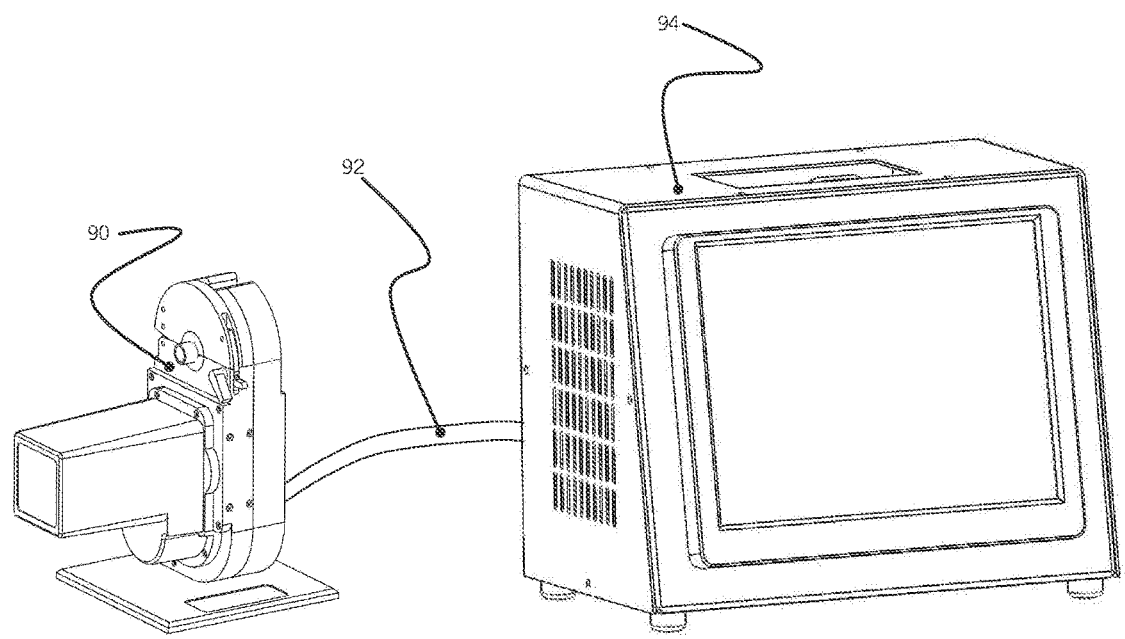
FIG. 14 is an isometric view of the head and computer control system.
Figure 15:
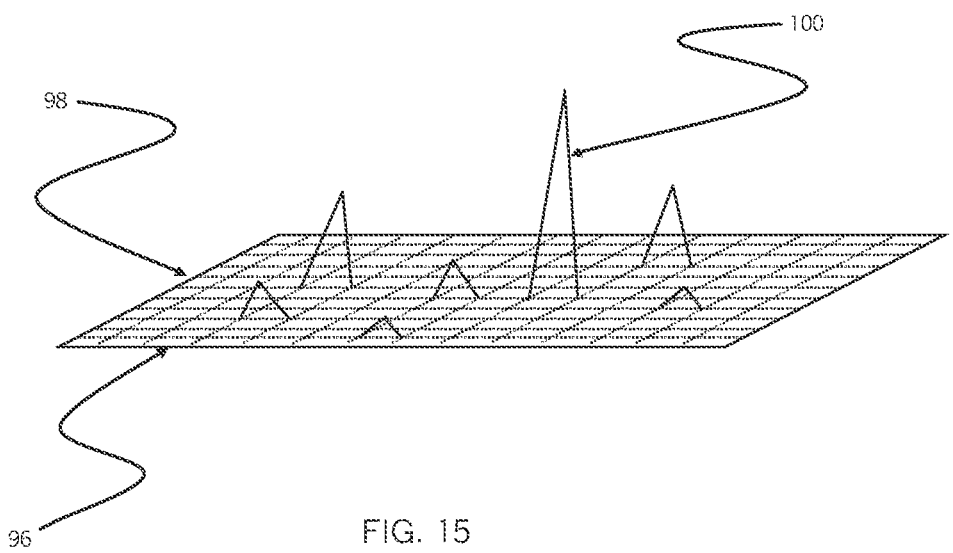
FIG. 15 is a view of an x, y or Cartesian coordinate data representation with sensing means data output as the z axis.

FIG. 14 illustrates the orbital weld inspection system being comprised of an orbital weld inspection head 90 a main power and signal control cable 92 and a controller with computer and graphical display 94. FIG. 15 illustrates a method of graphical display where previously described sensing means signal output may be correlated so as to match a particular rotational or translational location of orbital weld inspection head 90 or a series of locations such that 'x' axis 96 representing rotational movement of the orbital weld inspection head 90 with output data from said sensor collected at known intervals and being placed on the 'x' axis at intervals which match the distance traveled by said head over said interval and 'y' axis 98 representing the translational movement of the orbital weld inspection head 90 with output data from said sensor collected at known intervals being placed on the 'y' axis at intervals which match the distance traveled by said head having traveled over said interval and sensing means signal output 100 being displayed as the 'z' axis of the graphical display such that a topographical map of the weld joint assembly 1 is created.

Figure 16:
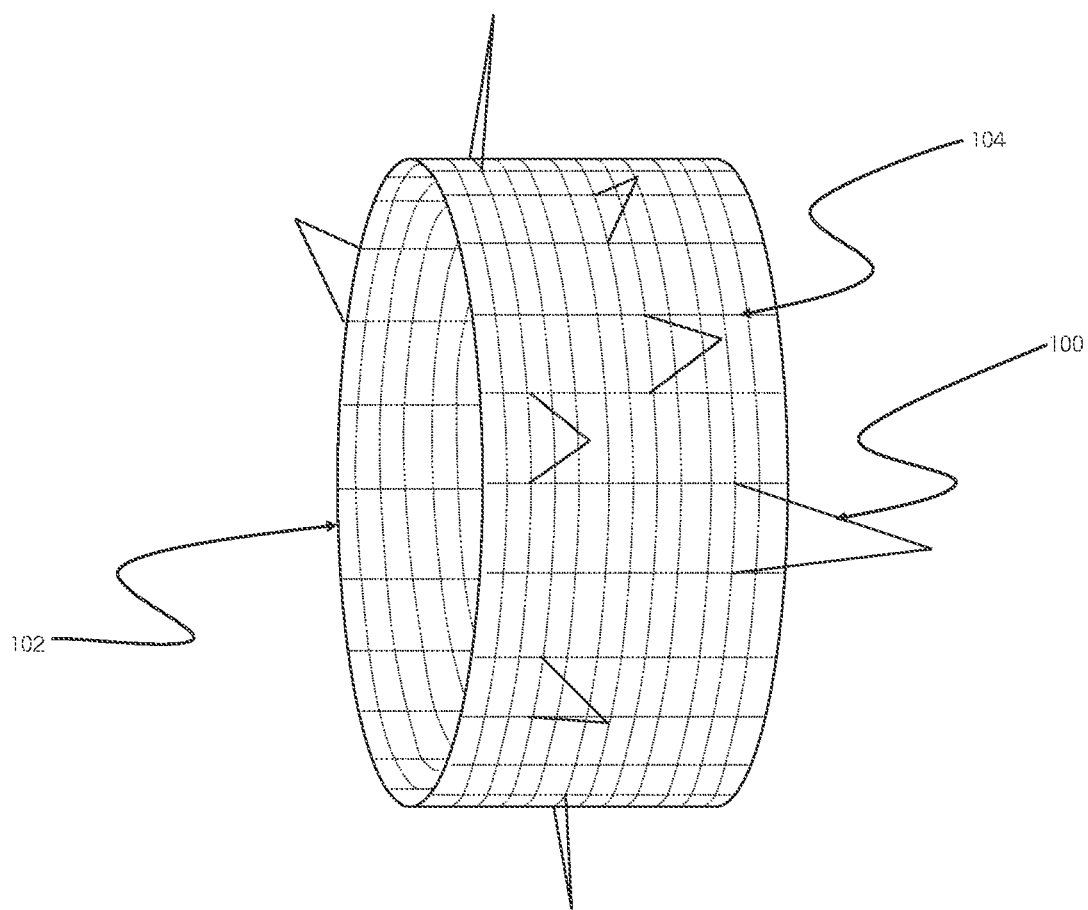
FIG. 16 is a view of a polar coordinate data representation with sensing means data output as the z or radial axis.

FIG. 16 illustrates a method of graphical display where previously described sensing means signal output may be correlated so as to match a particular rotational or translational location of orbital weld inspection head 90 or a series of locations such that rotational axis 102 representing rotational movement of the orbital weld inspection head 90 with output data from said sensor collected at known intervals and being placed on the rotational axis of the graph at intervals which match the distance traveled by said head over said interval and 'y' axis 98 representing the translational movement of the orbital weld inspection head 90 with output data from said sensor collected at known intervals and being placed on the 'y' axis of the graph at intervals which match the distance traveled by said head having traveled over said interval and sensing means signal output 100 being displayed as the radial axis of the graphical display such that a curvilinear topographical map of the weld joint assembly 1 is created.

Figure 17:
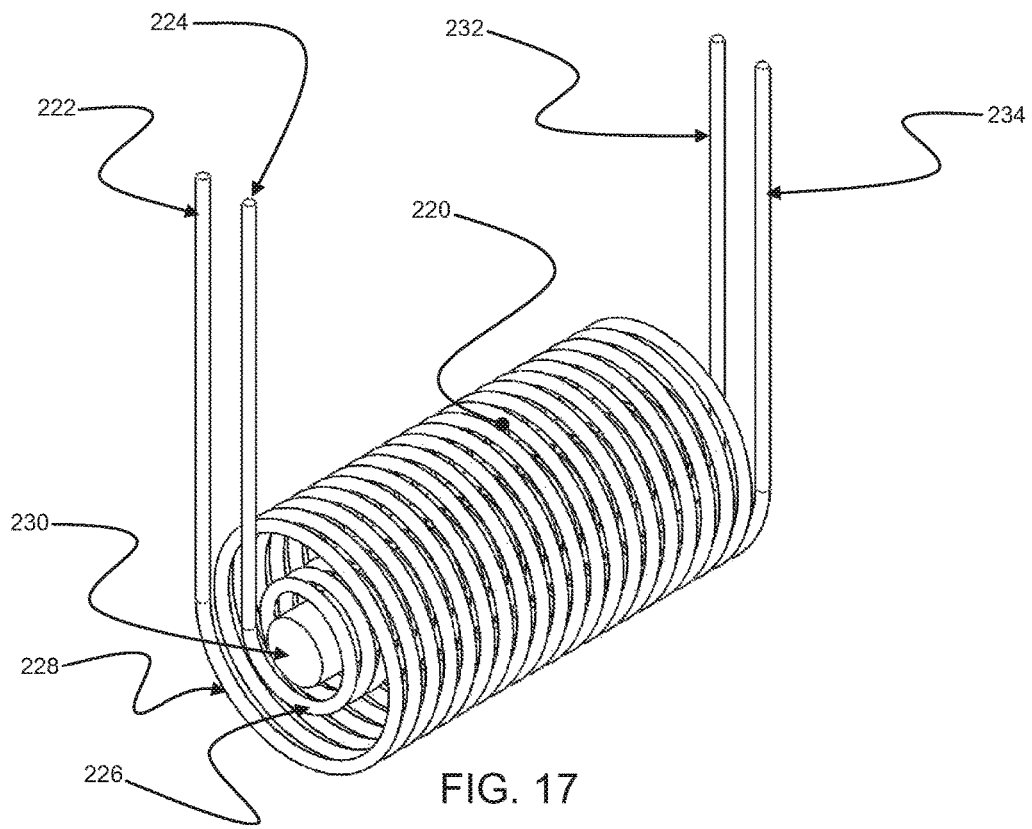
FIG. 17 is a perspective view of the resonant electromagnetic sensor constructed in accordance with this specification.

FIG. 17 is a preferred embodiment of the sensor assembly 220, comprised of a transmit coil 228 and a receive coil 226 concentrically arranged and with the receive coil 226 within the transmit coil 228. Within the receive coil is an optional core 230 made of material with high magnetic permeability and suitable for concentrating a magnetic field. This core serves to direct a greater amount of magnetic field to be generated by the transmit coil 228 into the area within the receive coil 226 so as to provide greater magnetic field to the receive coil 226. This magnetic field once concentrated within the receive coil 226 by way of the core 230 can be converted to an oscillating electromotive force or EMF in accordance with Lenz's Law. Also shown in this figure are the leads of the coils. The first lead of the transmit coil 222 and the second lead of the transmit coil 234 are to be energized with an oscillating electromotive force or EMF. The first lead of the receive coil 224 and the second lead of the receive coil 232 provide a signal output by converting an induced magnetic field to an EMF.

Figure 18:
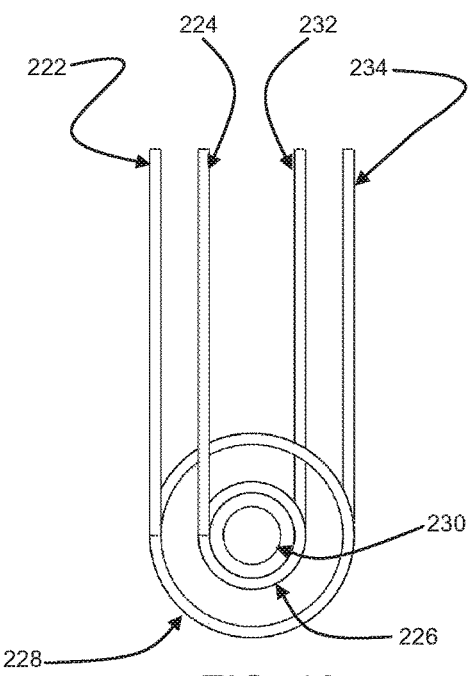
FIG. 18 is an orthographic end view of the sensor.

FIG. 18 is an end view of the sensor assembly showing the transmit coil 228 wound outside and concentric to the receive coil 226. There is a gap shown between the two coils as illustrated, but this gap can be very small or the two coils may be in contact with one another. There may even be materials used to separate the coils or a bobbin used to wind the transmit coil, which then becomes interposed between the two coils. Also visible in this figure is the core 230 of high permeability material meant to concentrate the magnetic field to be generated by the transmit coil 228.

Figure 19:
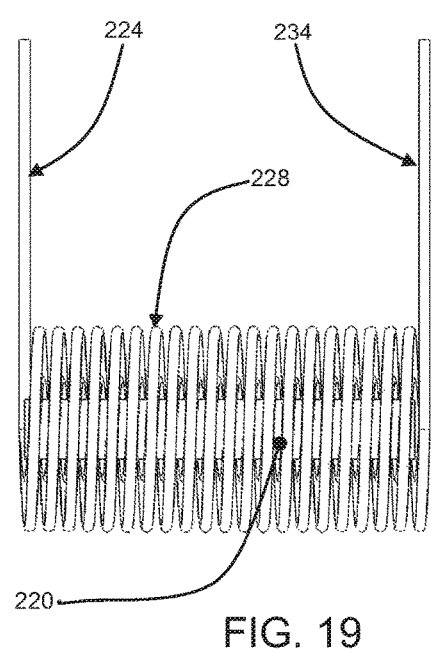
FIG. 19 is an orthographic side view of the sensor.

FIG. 19 shows the side view of the sensor and how the various components may be arranged within it. While the coils and the core are all of equal length, these lengths may be varied for ease of construction or to enhance performance. Also the number of turns on the transmit 228 and receive coil 226 may vary greatly. The number of turns selected for each will depend on several factors, such as the desired operating frequency, the desired energy transfer, and the desired amount of parasitic characteristics, or characteristics such as resistance, capacitance and inductance inherent in the winding itself.

Figure 20:
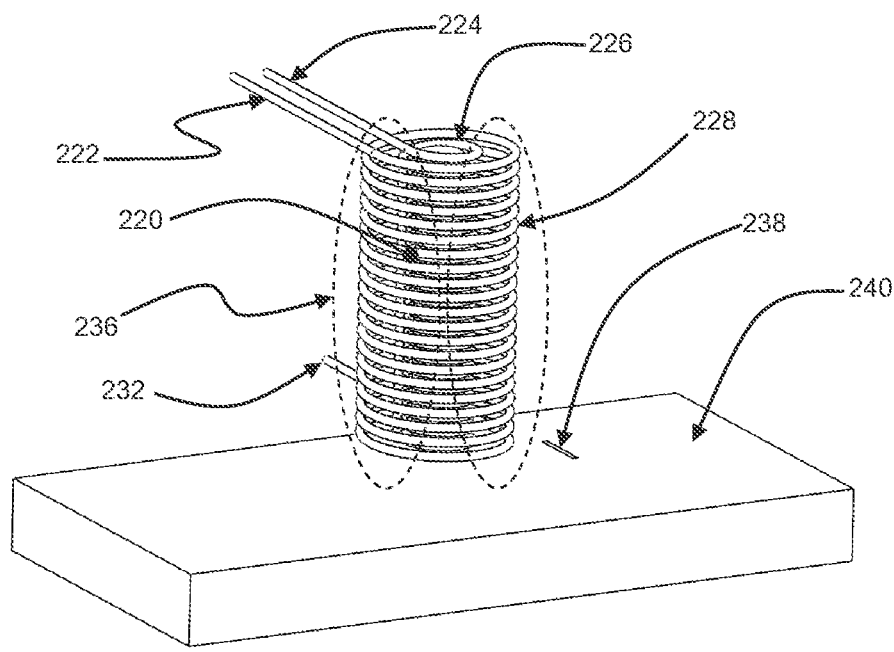
FIG. 20 is a perspective view of the sensor with a target material positioned in proximal to the sensor.

FIG. 20 shows the oscillating magnetic field 236 which has been generated by providing and oscillating EMF to the transmit coil 228. This magnetic field oscillates at a frequency which matches the oscillation applied to the leads 222 and 234 of the transmit coil 228. Placed in front of the sensor assembly 220, or in sensing proximity, is the target material 240, which may be made of conductive or nonconductive matter or a compound of materials. This matter or compound may be solid, liquid or gas as the sensor assembly 220 is capable of discerning characteristics for all of these states. For the sake of this explanation however, we will assume that this target material 240 is solid. Within or on the target material 240 is a discontinuity 238, which may be a flaw or a desired feature of either the same material of the target or different material. This discontinuity may be present on the surface closest to the sensor, within the target or on the side of the target farthest from the sensor assembly 220.

Figure 21:
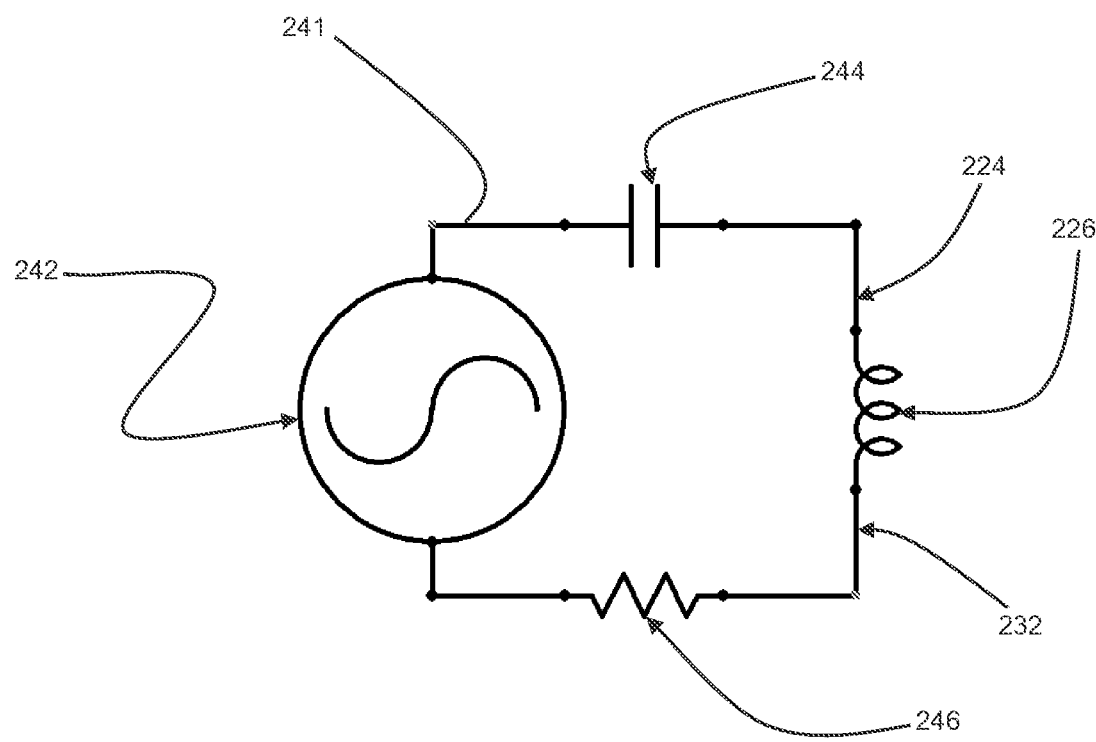
FIG. 21 is a schematic of transmit coil.

FIG. 21 is a schematic of the basic transmit coil circuit 241 and is shown to better understand the details of the sensor assembly 220. In this schematic, the source of oscillating EMF 242 can be seen as well as a classic LRC circuit taught in basic electronics. In this circuit there is a resistor 246, an inductor or transmit coil 226 and a capacitor 244. Transmit coil 226 having leads 224 and 232 connecting it to the circuit. It is well understood that in such a circuit the resonant frequency can be known by the formula $f=1/2\pi (LC)^{1/2}$. Where f is the resonant frequency of the transmit coil circuit 241 and L is the inductance of the transmit coil 228 and C is the transmit coil capacitor 244. It is important to note that while there is a resistor and capacitor shown, a contributing resistance and capacitance in the circuit can also be by way parasitic resistance and capacitance in the transmit coil 226. Also, while the resistance, inductance and capacitance in this circuit is shown in series, one or more of these elements could be in parallel arrangement. It is also useful to recognize that resonance is reached when inductive reactance $X_L$ is equal to and opposite capacitive reactance $X_C$ and since $XL=2\pi fL$ and $XC=1/2\pi fC$, it is easy to see how the formula for resonant frequency is derived.

While resistance is not shown in these formulas, it is an important component in the overall amplitude of the magnetic field 236 being created by the transmit coil 228. Altering either capacitance by way of changing the transmit coil capacitor 244 or the inductance of the transmit coil 228 has a dramatic effect on the resonant frequency of the circuit. Although it is not shown, inductance can be varied by adding an additional inductor or a variable inductor. However, the preferred embodiment is to vary the transmit coil capacitor 244 to tune resonant frequency as you might a radio receiver.

Figure 22:
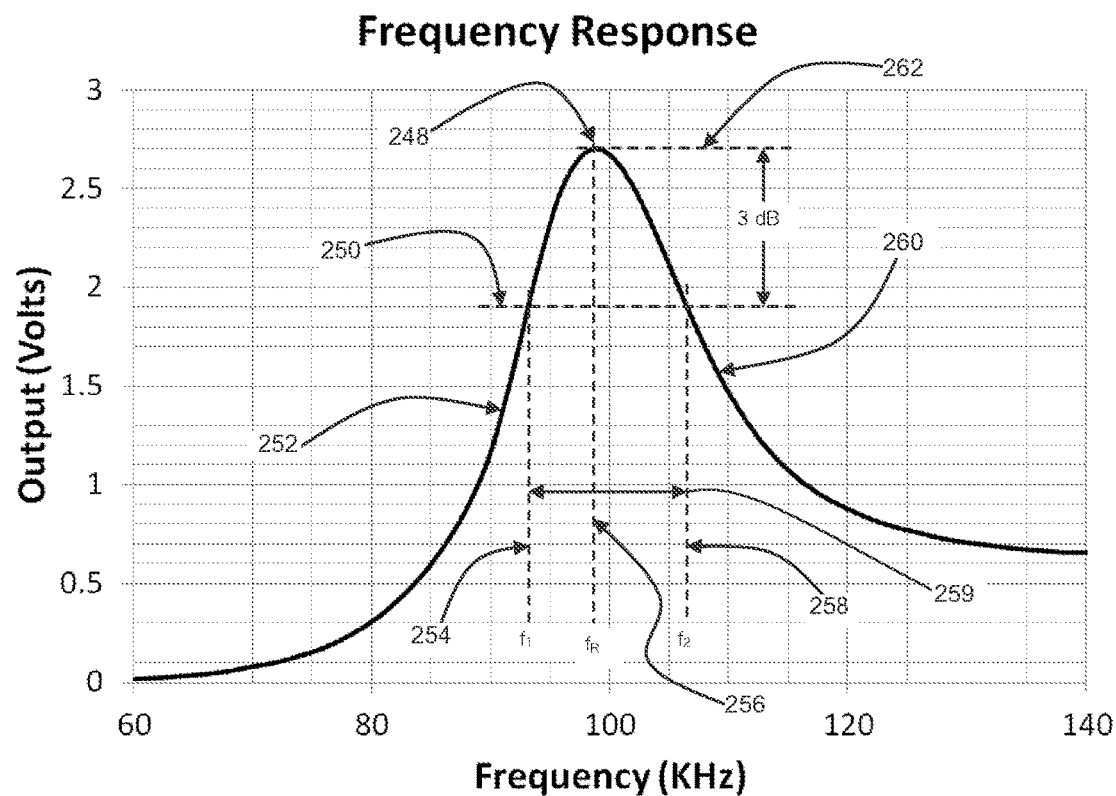
FIG. 22 is a frequency response graph of the transmit coil.

FIG. 22 shows the frequency response of a simple LRC circuit as with the transmit coil circuit 241 where there is a clear resonant peak 248 where $X_L$ is equal to $X_C$. It is clear that at frequencies below and above resonant frequency 256 the reactance increases and efficiency drops as is shown by the upslope side of the curve 252 as well as the downslope side of the curve 260. An important way to measure the quality of a resonating circuit or 'Q' is to divide the resonant frequency 256 by the bandwidth 259. Bandwidth 259 is given by measuring 3 dB down from the peak voltage at resonant frequency 262 to arrive at the voltage level at −3 dB 50. At that voltage level a horizontal line can be drawn 250 and where it intersects the frequency response curve two vertical lines can be drawn 254 and 258 where 254 is frequency 1 and 258 is frequency 2. By subtracting frequency 2, 258 from frequency 1, 254 bandwidth 259 can be known, or bandwidth=f2−f1. To calculate 'Q' the resonant frequency 256 is divided by the bandwidth 259. 'Q' will be used later in describing preferred operating frequencies of the sensor assembly 220.

Figure 23:
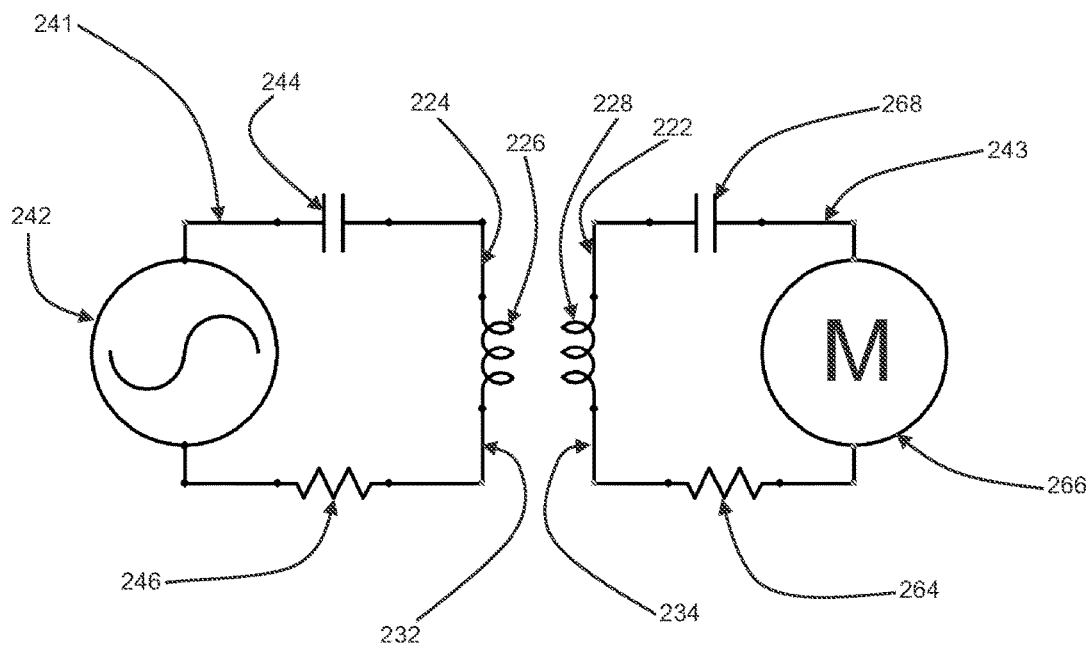
FIG. 23 is a schematic of the transmit coil and receive coil.

FIG. 23 shows a schematic of the transmit coil circuit 241 and the receive coil circuit 243. The receive coil 226, as mentioned, is collocated concentrically with and inside the transmit coil 228. Its purpose is to intercept the magnetic field 236 generated by the transmit coil 228 after having passed through the target material 240. It is preferred not to simply intercept the magnetic field 236, but rather to first tune the resonant frequency of the receive coil 226 to in some cases exactly match or have parity with the resonant frequency 256 of the transmit coil 226 and in other cases to be close to, or have approximate parity to the resonant frequency 256 of the transmit coil 226. This is done by again tuning receive coil circuit 243 by varying either inductance or the receive coil capacitor 268. In the preferred embodiment it is desirable to adjust or tune capacitance by varying the receive coil capacitor 268. As before variations in the receive coil resistor 264 serves to affect amplitude of the signal output. By tuning both the transmit circuit 241 and the receive coil circuit 243 to either parity or approximate parity, depending on the particulars of the circuit, an enhanced transmission of power can be realized from the transmit coil circuit 241 to the receive coil circuit 243.

Figure 31:
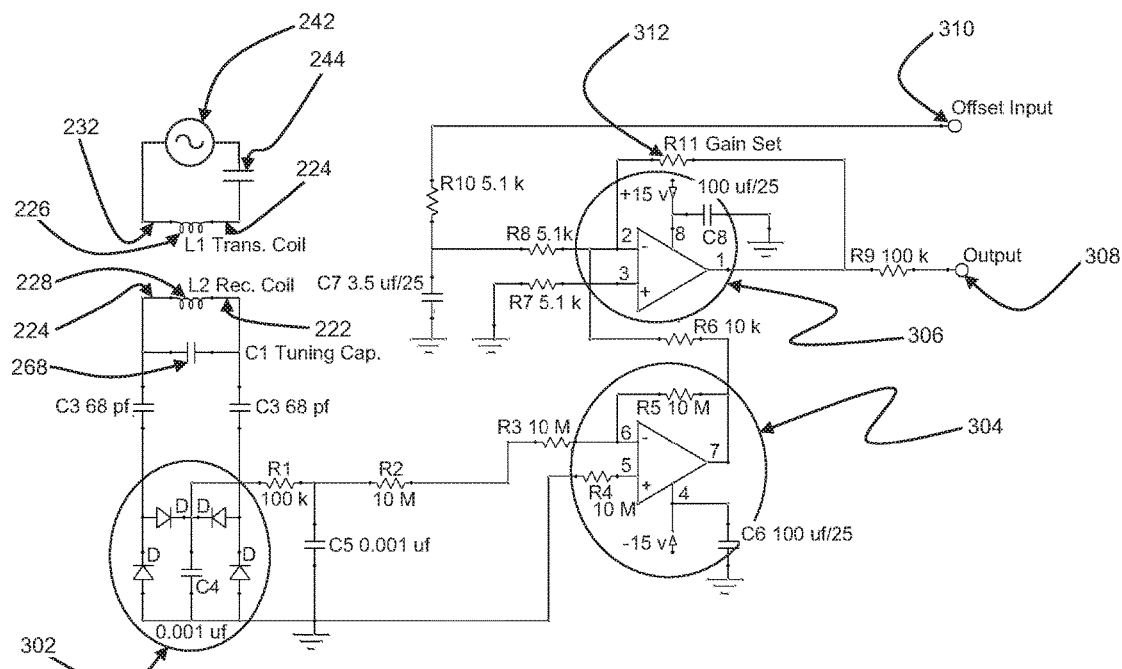
FIG. 31 is a schematic showing rectification and amplification of the receive coil output.

The energy transferred to the receive coil circuit 243 is monitored with signal monitoring and or conditioning device 266. This device may monitor the oscillating signal from the receive coil circuit with a display, commonly referred to as an impedance plane display, where impedance is given on an oscilloscope type device, where one axis of the display represents resistance of the circuit and the other axis represents inductive reactance. The preferred method of conditioning and monitoring in this embodiment which will be explained in FIG. 31 is rectification and then amplification of the DC signal. It is this preferred method that was used in the collecting of data for the frequency response curves in this specification.

Figure 24:
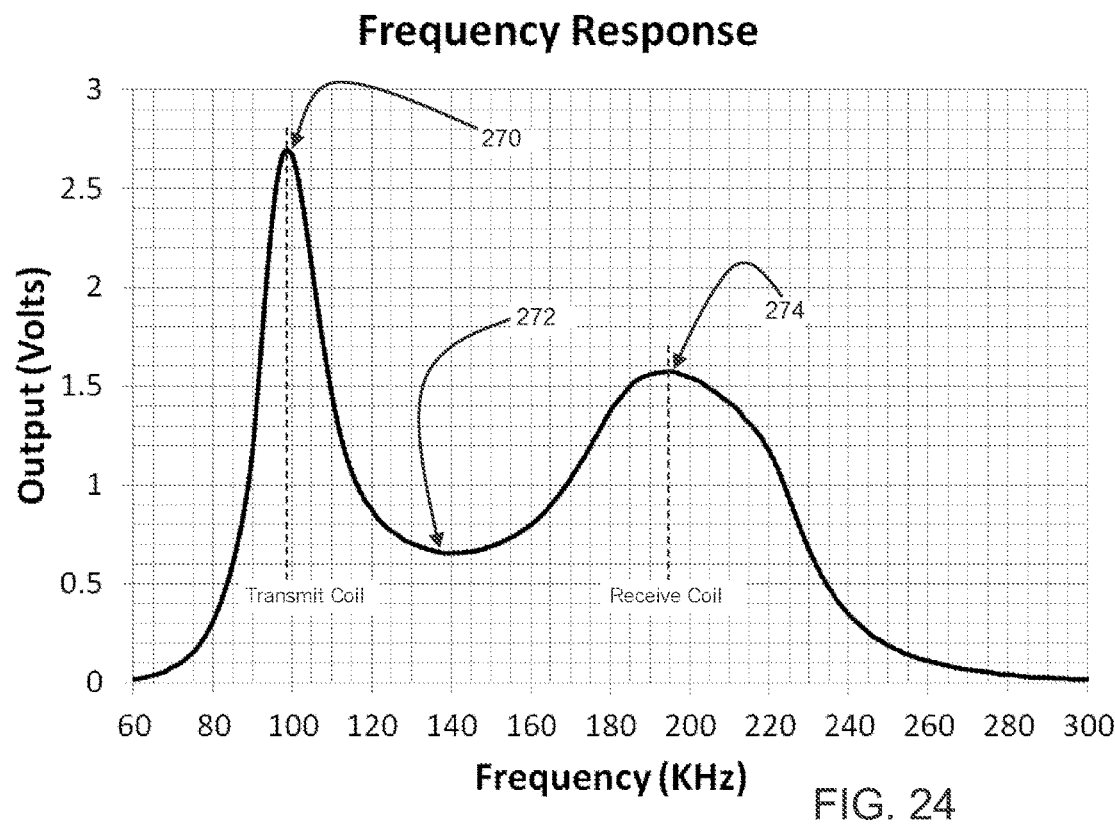
FIG. 24 is a frequency response graph of the transmit and receive coil.

FIG. 24 shows a frequency response of the circuit in FIG. 23 where the transmit coil circuit 241 has a resonant peak 270 which is at approximately 99 KHz and the receive coil circuit 243 has a receive coil resonant peak 274 which is approximately at 195 KHZ. While each of these peaks are at resonance and each is capable of detecting variations in material 240, this circuit has not been optimized. It can be seen that there is a trough 272 between the transmit coil resonant peak 270 and the receive coil resonant peak 274. This trough 272 is indicative of poor energy transfer from transmit coil circuit 241 and receive coil circuit 243 by way of transmit coil 226 and receive coil 228. It is desirable to minimize this trough 272 to enhance performance of the circuit of FIG. 23 and of the sensor assembly 220. This trough 272 can be minimized by proper tuning of the circuit of FIG. 23.

Figure 25:
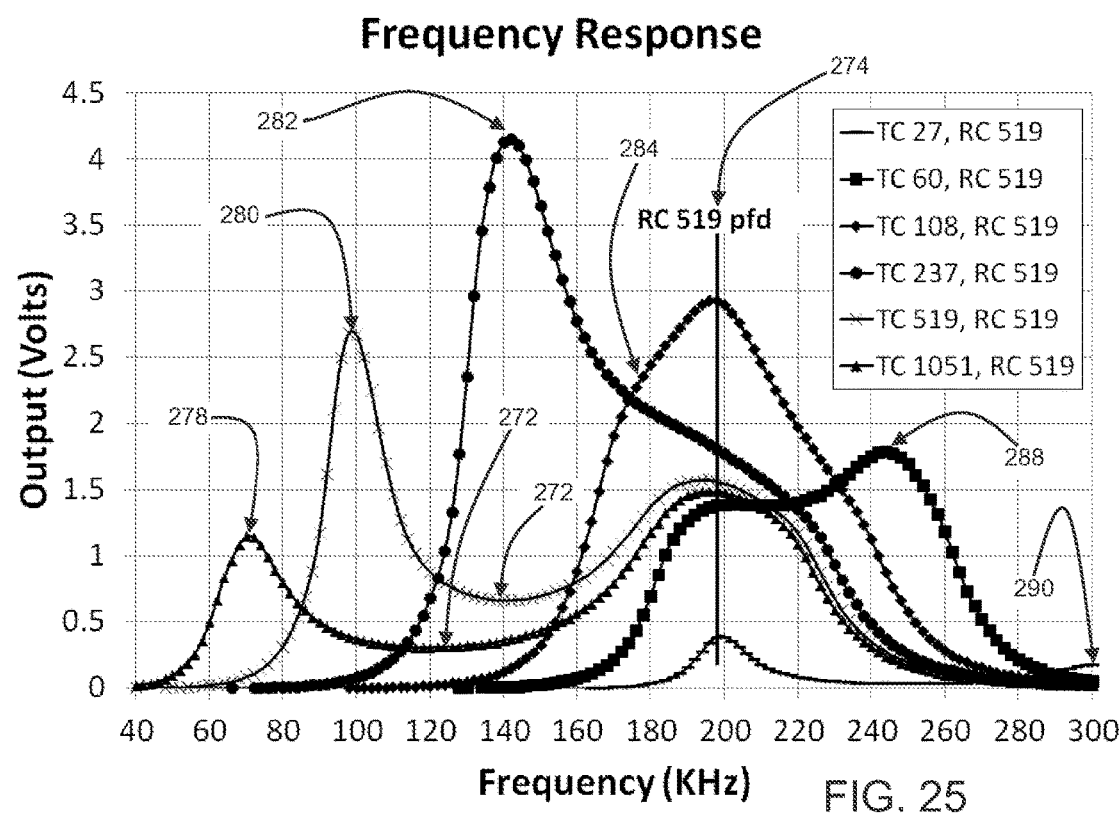
FIG. 25 is a frequency response graph showing sympathetic resonance.

FIG. 25 shows the frequency response of multiple variations of the circuit of FIG. 23, where the receive coil capacitor 268 has been set and held at 519 pfd (pico farads) giving a receive coil resonant peak 274 of about 195 KHz. It can be seen that as the transmit coil capacitor 244 of the transmit coil circuit 241 is changed to different values there is a dramatic effect on frequency response. It can be seen that a transmit coil first resonant peak 278 with a transmit coil capacitor 244 of 1052 pfd is far removed from the receive coil resonant peak 274 and transfers a low amount of energy from the transmit coil circuit 241 to the receive coil circuit 243 and that the trough 272 is quite wide. The transmit coil second resonant peak 280 has greatly improved in amplitude by using a transmit coil capacitor 244 of 519 pfd. This has brought its resonant peak 280 closer to the receive coil resonant peak 274 and in so doing has boosted energy transfer by improving "sympathetic resonance", where the resonant frequency of the transmit coil is either in parity with or in approximate parity to the resonant frequency of the receive coil such that output is increased beyond the output of the constituent resonant peaks. Maximum output of this particular circuit of FIG. 23 reaches its maximum when the transmit coil capacitor 244 is set at 237 pfd, yielding sympathetic resonant peak 282. At this frequency of about 142 KHz, the circuit will be most sensitive to changes in target material 240 and will be most able to detect variations such as discontinuities in target material 238. In this case, this peak occurred at an approximate parity frequency which does not match the receive coil resonant peak 274. This is due to a wide variety of reasons from the construction of the sensor assembly 220 to the particular tuning of the circuit of FIG. 23. Depending on construction and tuning, the sympathetic resonant peak could be at frequencies lower than, greater than or equal to the receive coil resonant peak 274. Transmit coil fourth, fifth and sixth resonant peaks 284, 288 and 290, respectively, occur at different frequencies but are not optimized.

Figure 26:
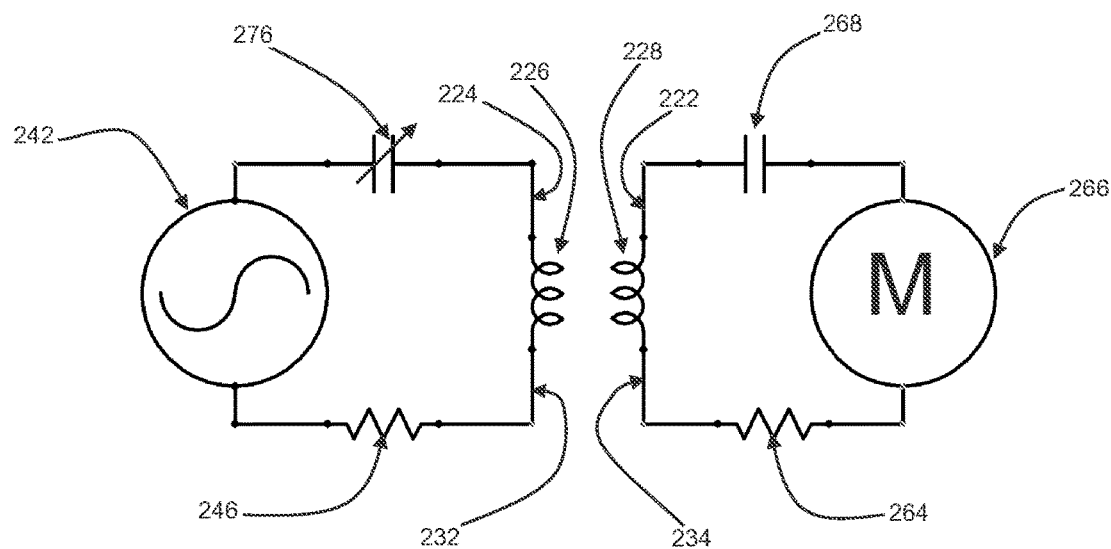
FIG. 26 is a schematic of the transmit and receive coils where the transmit capacitance is variable.
Figure 27:
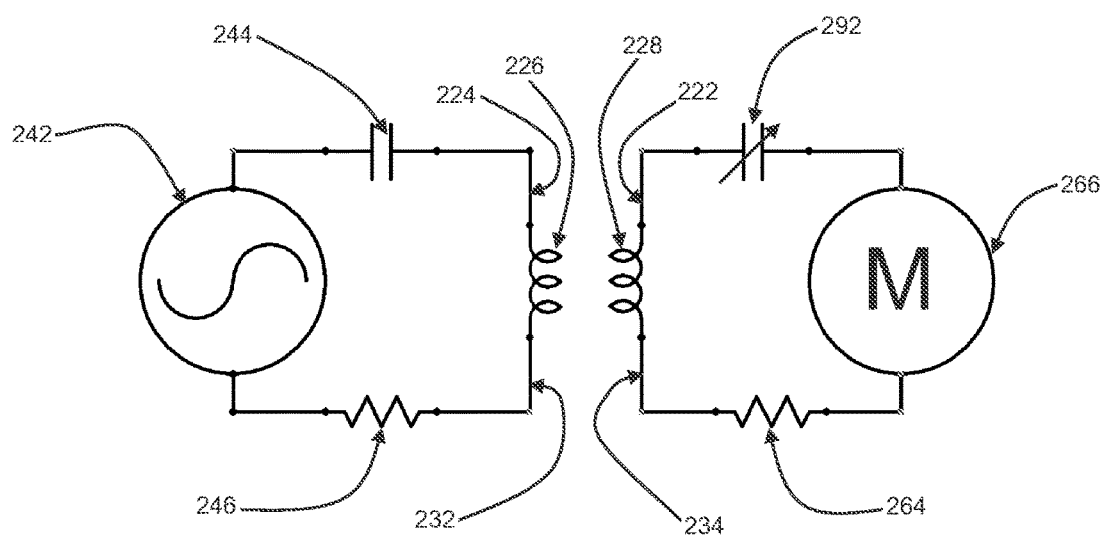
FIG. 27 is a schematic of the transmit and receive coils where the receive capacitance is variable.
Figure 28:
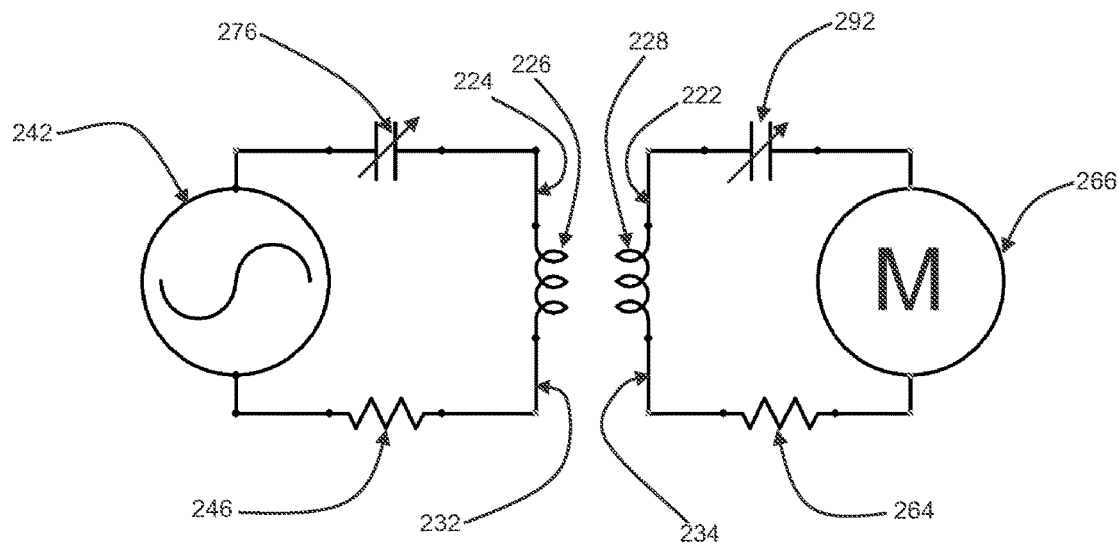
FIG. 28 is a schematic of the transmit and receive coils where both receive and transmit capacitance are variable.

FIGS. 26, 27 and 28 show the addition of variable capacitors to either the transmit coil circuit 241 or the receive coil circuit 243 or both. FIG. 26 shows transmit coil capacitor 244 being replace with transmit coil variable capacitor 276. FIG. 27 shows receive coil capacitor 268 being replaced by receive coil variable capacitor 292 and FIG. 28 shows both the transmit coil capacitor 244 and the receive coil capacitor 268 being replace by transmit coil variable capacitor 276 and receive coil variable capacitor 292 respectively. These aforementioned variable capacitors may be manually variable or variable by electronic signal. The purpose of these variable capacitors is to allow rapid switching to other desired resonant peaks or sympathetic resonant peaks in order to more thoroughly inspect the target material 240.

Figure 29:
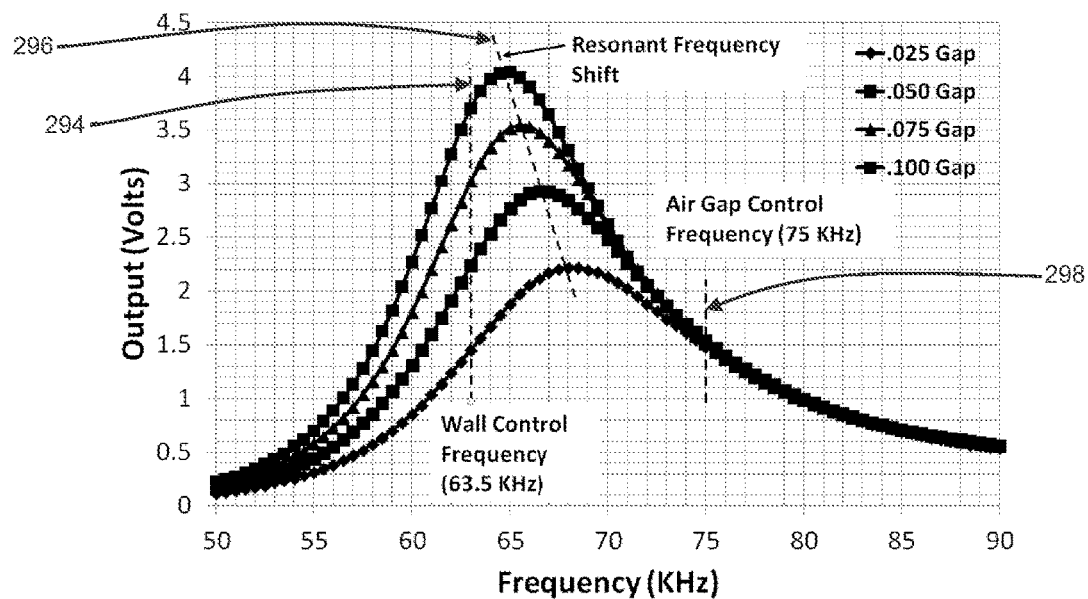
FIG. 29 is a frequency response graph showing an air gap control frequency.

FIG. 29 shows a circuit tuned to a resonant frequency which may or may not be the sympathetic resonant frequency, where desirable characteristics other than maximum power transfer or maximum output occur. This tuning may be achieved by adjusting one or more variable capacitors such as in the circuits of FIG. 26, 27 or 28.

It is often a desirable feature of a sensor to be able to control for variables such as liftoff, the gap or distance from the sensor assembly 220 to the target material 240, or changes in material configuration such as the wall thickness of that material. FIG. 29 shows how the control of gap may be accomplished by monitoring the output of the circuit at the air gap control frequency 298 of 75 KHz as opposed to the resonant peak. In doing this, it can be seen that the effects of gap are greatly mitigated relative to other frequencies.

Figure 30:
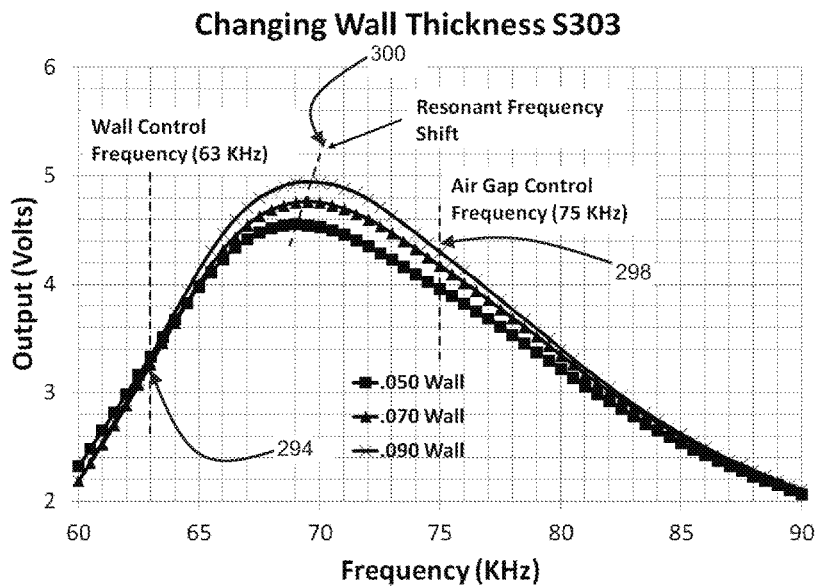
FIG. 30 is a frequency response graph showing a wall control frequency.

The same circuit is shown in FIG. 30, but instead of varying gap, the wall thickness of the material is varied. It can be seen that the air gap control frequency 298, which mitigates changes in gap, is sensitive to changes in wall. This means that even though there are changes in the distance from the sensor to the target, those changes are mitigated while the effects of varying wall can be clearly seen.

Similarly, at the wall control frequency 294 of 63 KHz, as wall is varied the signal is mitigated, but as gap is varied, the signal output changes appreciably. In this manner the sensor assembly 220 may be tuned to control variables and or tuned to provide maximum output and frequencies may be switched as desired to achieve maximum signal or mitigated signal. While the control signals for wall and gap have been shown, other control frequencies exist to mitigate change in material or change in temperature which are found by similar tuning methods.

Further studying the frequency response curve of FIG. 29, it can be appreciated that the compression of curves at and about the air gap control frequency 298 and the subsequent expansion of curves at the wall control frequency 294 occurs as a result of a resonant frequency shift for air gap 296. It can be seen that as air gap increase the signal amplitude rises while the resonant frequencies shift lower. This is true of this particular tuning setting and the phenomena may be reversed if tuned differently where the resonant frequency shift for air gap may be to higher frequencies, causing a reversal in the compression and expansion of the curves and or causing a reduction in signal due to increased air gap.

Conversely, in FIG. 30 as wall thickness changes the resonant frequency shift for wall 300 is to higher frequencies as wall thickness increases and signal increases as wall increases. This causes a compression of the curves at the wall control frequency 294 and an expansion of the curve at the air gap control frequency 298. Again, depending on tuning, these compression and expansion areas may be reversed and signal may diminish relative to wall.

FIG. 31 shows a preferred embodiment of the signal monitoring and or conditioning device 266, where the output of the receive coil circuit 243 is fed into a rectifier circuit 302 to convert the oscillating signal to a DC or direct current output. The DC signal is then fed into an amplifier first stage 304 where the signal is amplified. The amplified signal is then sent to the amplifier second stage 306, where additional amplification may be accomplished by setting or adjusting gain resistor 312. Often, there is a computer which will receive the output 108 of the signal monitoring and or conditioning device 266 and FIG. 31, as many computers can tolerate a relatively narrow voltage input of perhaps +/−10 volts. Should the signal become too large due to amplification, resonant tuning or high voltage being delivered by source of oscillating EMF 242, an offset input 310 may be applied. In so doing the output voltage is shifted to a lower voltage which can be received by the computer while preserving any effects that may have come about by monitoring variations in target material 240.

What is claimed is:

1. An orbital device for rotation about a tubular workpiece, the orbital device comprising:
   a rotating member comprising an axial opening, a radial opening, a plurality of gear teeth formed about at least part of a circular sector, the rotating member being circular and rotating about an axis of rotation, the rotating member being rotated by a motor through one or both of a first tandem gear and a second tandem gear;
   a tool extending inwardly from the axial opening of the rotating member;
   the rotating member being rotatable to move the tool through an arcuate path about the tubular workpiece;
   a translating member movable in a linear direction along the axis of rotation, the rotating member mounted on the translating member and moving in the linear direction with the translating member; and a housing supporting the translating member which is translatable relative to the housing.

2. The orbital device of claim 1 further comprising a fixture clamp which closes to securely grip the tubular workpiece, such that the tubular workpiece is fixed in relation to the housing.

3. The orbital device of claim 1 wherein the tool is a sensor device comprising:
   a transmit coil being tuned to a desired resonant frequency by inducing an oscillating electromotive force for creating an oscillating magnetic field at the desired resonant frequency, the oscillating magnetic field being configured to propagate into the tubular workpiece; and
   a receive coil receiving the oscillating magnetic field with a resonant frequency which is in proximity to the desired resonant frequency of the transmit coil such that the output signal of the receive coil is improved for desired detection of features, flaws, and conditions of the tubular workpiece.

4. The orbital device of claim 3 wherein the rotating member further comprises a cable groove formed about the rotating member and as the rotating member rotates a cable is received within the cable groove, the cable in electrical communication with the tool.

5. The orbital device of claim 4 wherein the control cable is further reeled about a second wire spool, the second wire spool being biased to wind the signal and power cable about the second wire spool.

6. The orbital device of claim 5 wherein a slip ring is connected to the second wire spool, the slip ring providing a rotating electrical connection from the transmit coil and the receive coil to a computing device.

7. The orbital device of claim 3 wherein the receive coil is inserted within the transmit coil.

8. The orbital device of claim 7 wherein a core is inserted within the receive coil, the core being made of a material with high magnetic permeability.

9. An orbital device for rotation about a tubular workpiece, the orbital device comprising:
   a rotating member comprising an axial opening;
   a rotating member comprising an axial opening, a radial opening, a plurality of gear teeth formed about at least part of a circular sector, the rotating member being circular and being rotated by a motor through one or both of a first tandem gear and a second tandem gear;
   a tool extending inwardly from the axial opening of the rotating member, the rotating member being rotatable about an axis of rotation to move the tool through an arcuate path about the tubular workpiece;
   a translating member movable in a linear direction along the axis of rotation, the rotating member mounted on the translating member and moving in the linear direction with the translating member;
   a housing supporting the translating member which is translatable relative to the housing; and
   a fixture configured to securely hold the tubular workpiece relative to the housing.

10. The orbital device of claim 9 wherein the fixture is an integral part of the housing.

11. The orbital device of claim 9 wherein the tool is a sensor device comprising:
   a transmit coil being tuned to a desired resonant frequency by inducing an oscillating electromotive force for creating an oscillating magnetic field at the desired resonant frequency, the oscillating magnetic field being configured to propagate into the tubular workpiece; and
   a receive coil receiving the oscillating magnetic field with a resonant frequency which is in proximity to the desired resonant frequency of the transmit coil such that the output signal of the receive coil is improved for desired detection of features, flaws, and conditions of the tubular workpiece.

* * * * *